US009528138B2

(12) United States Patent
Weissman et al.

(10) Patent No.: US 9,528,138 B2
(45) Date of Patent: Dec. 27, 2016

(54) METHOD FOR DISCOVERING ALGAL STRAINS WITH REDUCED PIGMENT TO ATTAIN HIGHER PHOTOSYNTHETIC EFFICIENCY

(71) Applicants: Joseph Charles Weissman, Annandale, NJ (US); Robert David Nielsen, Lambertville, NJ (US); Roger Charles Prince, Pittstown, NJ (US)

(72) Inventors: Joseph Charles Weissman, Annandale, NJ (US); Robert David Nielsen, Lambertville, NJ (US); Roger Charles Prince, Pittstown, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 210 days.

(21) Appl. No.: 14/284,600

(22) Filed: May 22, 2014

(65) Prior Publication Data

US 2014/0356902 A1   Dec. 4, 2014

Related U.S. Application Data

(60) Provisional application No. 61/830,909, filed on Jun. 4, 2013.

(51) Int. Cl.
| | | |
|---|---|---|
| *C12Q 1/02* | (2006.01) | |
| *C12N 1/12* | (2006.01) | |
| *C12N 1/36* | (2006.01) | |
| *C12Q 1/04* | (2006.01) | |

(52) U.S. Cl.
CPC . *C12Q 1/02* (2013.01); *C12N 1/12* (2013.01); *C12N 1/36* (2013.01); *C12Q 1/04* (2013.01)

(58) Field of Classification Search
CPC .............. C12N 15/01; C12N 1/12; C12Q 1/02
See application file for complete search history.

(56) References Cited

FOREIGN PATENT DOCUMENTS

| WO | 2006020177 | 2/2006 |
|---|---|---|
| WO | 2013013139 | 1/2013 |

OTHER PUBLICATIONS

Melis, A., Plant Science (2009); vol. 177, pp. 272-280.*
Huesemann, M. et al. (2009) Appl. Biochem. Biotechnol.,vol. 157, pp. 507-526.*
Nakajima, Y. et al. (2001) Journal of Applied Phycology, vol. 13, pp. 95-101.*
Falkowski, et al., "Growth-irradiance relationships in phytoplankton", American Society of Limnology and Oceanography, 1985, vol. 30, iss. 2, pp. 311-321, University Press of New England.
Morel, et al., "Inherent Optical Properties of Algal Cells Including Picoplankton: Theoretical and Experimental Results", Canadian Bulletin of Fisheries and Aquatic Sciences, 1986, No. 214, pp. 517-559.
Ley, Relationships among cell chlorophyll content, photosystem II light-harvesting and the quantum yield for oxygen production in Chlorella, Photosynthesis Research, 1986, vol. 10, pp. 189-196, Springer.
Chow, et al., "Adjustments of Photosystem Stoichiometry in Chloroplasts Improve the Quantum Efficiency of Photosynthesis", Proceedings of the National Academy of Sciences of the USA, Oct. 1990, vol. 87, No. 19, pp. 7502-7506, National Academy of Sciences.
Nakajima et al., "Improvement of photosynthesis in dense microalgal suspension by reduction of light harvesting pigments", Journal of Applied Phycology, 1997, vol. 9, pp. 503-510, Kluwer Academic Publishers, Netherlands.
Kolber et al., "Measurements of variable chlrorophyll fluorescence using fast repetition rate techniques: defining methodology and experimental protocols", Biochemica et Biophysica Acta, 1998, vol. 1367, pp. 88-106, Elsevier.
Nakajima et al., "The effect of reducing light-harvesting pigment on marine microalgal productivity", Journal of Applied Phycology, 2000, vol. 12, pp. 285-290, Kluwer Academic Publishers, Netherlands.
Baker, "Chlorophyll fluorescence: a probe of photosynthesis in vivo", Annual Review of Plant Biology, 2000, vol. 59, pp. 89-113, Annual Reviews.
Nakajima, et al., "Improved productivity by reduction of the content of light-harvesting pigment in Chlamydomonas perigranulata", Journal of Applied Phycology, 2001, vol. 13, pp. 95-101, Kluwer Academic Publishers, Netherlands.
Wu et al., "A model integrating fluid dynamics in the photosynthesis and photoinhibition process", Chemical Engineering Science, 2001, vol. 56, pp. 3527-3538, Pergamon, Elsevier.
Pruvost et al., "Simulation of Microalgae Growth in Limiting Light Conditions: Flow Effect", AIChE Journal, May 2002, vol. 48, No. 5, pp. 1109-1120, John Wiley & Sons, Inc.
Nakajima et al., "Analysis of photosynthetic productivity of microalgal mass cultures", Journal of Applied Phycology, 2003, vol. 15, pp. 497-505, Kluwer Academic Publishers, Netherlands.
Polle, et al., "tla1, a DNA insertional transformant of the green alga Chlamydomonas reinhardtii with a truncated light-harvesting chlorophyll antenna size." Planta, 2003, vol. 217, pp. 49-59, Springer-Verlag.
Luo et al., "Analyzing and Modeling of Photobioreactors by Combining First Principles of Physiology and Hydrology", Biotechnology and Bioengineering, 2004, vol. 85, pp. 382, Wiley Periodicals, Inc.
Perner-Nochta et al., "Simulations of light intensity variation in photobioreactors", Journal of Biotechnology, 2007, vol. 131, pp. 276-285, ScienceDirect, Elsevier.

(Continued)

*Primary Examiner* — Russell Kallis
(74) *Attorney, Agent, or Firm* — David M. Weisberg

(57) ABSTRACT

A method for determining and/or engineering photosynthetic mutant algal strains comprising: (A) pre-screening wild-type or parent strains to select for photosynthetic efficiency; (B) cause genetic mutations in the group of wild-type and/or parent strains from pre-screening (A) to form genetic mutant strains; (C) screening the genetic mutant strains for photosynthetic efficiency in mass cultures; and (D) further screening the genetic mutants resulting from screening (C) by measuring biomass productivity to select strains having relatively high biomass/lipid/starch productivity.

6 Claims, No Drawings

(56) References Cited

OTHER PUBLICATIONS

Sastre et al., "Scale-down of microalgae cultivations in tubular photobioreactors—A conceptual 15 approach", Journal of Biotechnology, 2007, vol. 132, pp. 127-133, ScienceDirect, Elsevier.

Mussgnug, et al., "Engineering photosynthetic light capture: impacts on improved solar energy to biomass conversion", Plant Biotechnology Journal, 2007, vol. 5, pp. 802-814, Blackwell Publishing Ltd.

Tetali et al., "Development of the light-harvesting chlorophyll antenna in the green alga Chlamydomonas reinhardtii is regulated by the novel Tla1 gene", Planta, 2007, vol. 225, No. 4, pp. 813-829, Springer-Verlag.

Nedbal et al., "A photobioreactor system for precision cultivation of photoautotrophic microorganisms and for high-content analysis of suspension dynamics", Biotechnology and Bioengineering, Aug. 1, 2008, vol. 100, No. 5, Wiley Periodicals, Inc.

Gaigalas, et al., "Measurement of Absorption and Scattering With an Integrating Sphere Detector: Applications to Microalgae", Journal of Research of the National Institute of Standards and Technology, Mar.-Apr. 2009, vol. 114, No. 2, pp. 69-81, U.S. Deptarmtne of Commerce.

Beckman et al., "Improvement of light to biomass conversion by de-regulation of light-harvesting protein translation in Chlamydomonas reinhardtii", Journal of Biotechnology, 2009, vol. 142, pp. 70-77, ScienceDirect, Elsevier.

James et al., "Modeling Algae Growth in an Open-Channel Raceway", Journal of Computational Biology, 2010, vol. 17, No. 7, pp. 895-906, Sandia National Laboratories.

Sato et al., "Development of virtual photobioreactor for microalgae culture considering turbulent flow and flashing light effect", Energy Conversion and Management, 2010, vol. 51, pp. 1196-1201, Pergamon, Elsevier.

Zhu et al., "Improving photosynthetic efficiency for greater yield", Annual Review of Plant Biology, Mar. 1, 2010, vol. 61, pp. 235-261, Annual Reviews.

Ort, et al., "Optimizing antenna size to maximize photosynthetic efficiency." Plant Physiology, Jan. 2011, vol. 155, pp. 79-85, American Society of Plant Biologists.

Branyikova, et al., "Microalgae—Novel highly efficient starch producers", Biotechnology and Bioengineering, Apr. 2011, vol. 108, No. 4, pp. 766-776, Wiley Periodicals, Inc.

Pinchasov-Grinblat, et al., "The effect of photoacclimation on photosynthetic energy storage efficiency, determined by photoacoustics", Open Journal of Marine Science, Jul. 2011, vol. 1, No. 2, pp. 43-49, Scientific Research.

Bonente, et al., "Acclimation of Chlamydomonas reinhardtii to different growth irradiances", The Journal of Biological Chemistry, Feb. 17, 2012, vol. 287, No. 8, pp. 5833-5847, American Society for Biochemistry and Molecular Biology.

Kirst, et al., "Truncated photosystem chlorophyll antenna size in the green microalga Chlamydomonas reinhardtii upon deletion of the TLA3-CpSRP43 gene", Plant Physiology, Dec. 2012, vol. 160, No. 4, pp. 2251-2260, American Society of Plant Biologists.

Kandilian, et al., "Radiation and optical properties of Nannochlropsis oculata grown under different irradiances and spectra", Bioresource Technology 2013, vol. 137, pp. 63-73, Elsevier.

International Search Report with Written Opinion from PCT/2012/047578 dated May 14, 2013.

* cited by examiner

METHOD FOR DISCOVERING ALGAL STRAINS WITH REDUCED PIGMENT TO ATTAIN HIGHER PHOTOSYNTHETIC EFFICIENCY

CROSS-REFERENCE TO RELATED APPLICATIONS

This application claims the benefit of U.S. Application Ser. No. 61/830,909, filed on Jun. 4, 2013; which is incorporated by reference herein in its entirety.

FIELD OF THE INVENTION

The invention relates to methods of screening for photosynthetic algal strains/mutants having desirable properties, as well as to paths toward selecting and/or engineering photosynthetic algal strains/mutants having said desirable properties.

BACKGROUND OF THE INVENTION

Most mass algal cultures are operated at high enough cell density that the response of each cell is influenced by shading; one way they respond is by making additional pigment in order to be competitive in the low average light environment of the culture. Typically, the chlorophyll a content in mass algal cultures is 2-3% of the cellular mass. In such mass cultures, the cells are exposed to high light in the regions of the culture closest to the light source. Here the light is absorbed faster than it can be processed by the cell, leading to photosynthetic inefficiency.

Many efforts have been made to increase the photosynthetic efficiency, and hence the biomass productivity, of mass algal cultures through manipulation of the algal light harvesting apparatus to bring light absorption in high light into balance with the rate at which the algal cell's metabolic apparatus can process the products of the light-induced charge separation and carbon dioxide into cell mass. Normally, the imbalance under high light causes the dissipation of absorbed photon energy into heat, and as much as 90% of the photons can be wasted in this manner. This is often called light saturation.

One common way to overcome light saturation and increase photosynthetic biomass productivity is to reduce the cell's capacity to absorb light by reducing the cellular content of pigment, particularly of chlorophyll. This is typically done by inducing genetic changes and selecting cells that have tested characteristics that tend to correlate with higher productivity. Unfortunately, many times, the selected variants do not exhibit high enough efficiency under high light.

Currently various screening protocols are used to select from thousands (or more) of genetically altered variants of an algal strain to discern the few that possess criteria that one would expect to lead to greater biomass productivity under high incident light by overcoming saturation effects that waste photons. These screens include: visual or optical discrimination of low chlorophyll variants; selection of these strains; growth in low light to assure that the low chlorophyll change endures; assessment of some measure of the light intensity of saturation; and some measure of the maximum photosynthetic rate, all to assure similarity to the parent strain. These screens do not assure that the parent strain is efficient itself.

What is needed is an improved screening procedure that takes into consideration not only photosynthetic efficiency but also increased biomass/lipid/starch productivity and/or production efficiency.

SUMMARY OF THE INVENTION

One purpose of this invention is to increase the success rate of the generation of high efficiency low chlorophyll strains. This can be achieved by beginning with a very efficient algal strain (assessed in low light) and altering the pigment content to a great enough degree to change the cellular light absorption characteristics without damaging the efficiency of this variant in low light. The inventive process can advantageously result in photosynthetic efficiency and hopefully also productivity increases (e.g., by at least 50%, and up to about 300%) in algal cultures exposed to high incident light intensity.

DETAILED DESCRIPTION OF THE EMBODIMENTS

There are many factors that can be measured to assess the efficiency of photosynthesis (in native and altered strains) directly. For instance, one can be to simply grow a dense culture under relatively high intensity incident light, estimate the light absorption, and measure the biomass productivity. This is not normally used as a screening protocol for the large number (at least thousands) of strains produced by mutagenesis, or other genetic alteration, because it can be prohibitively labor intensive. This method can, however, be used as an ultimate validation that increases in biomass productivity have been achieved by a short list of strains remaining after the plethora produced by methods used to alter cellular pigment content have been screened.

Indeed, in typical processes, strains of interest can be mutagenized, or otherwise genetically altered, to produce quite a large number (e.g., thousands) of mutants, which can then be screened to identify the relative few having putatively higher efficiency. This whole process is typically very time consuming and costly.

According to one aspect of the present invention, a less time consuming, less labor intensive, and less costly screening method is devised. First, strains can be pre-screened to judge their ability and/or propensity for increased photosynthetic productivity. One non-limiting pre-screening method step can be to measure a minimum quantum requirement (the minimum number, or quanta, of photons/incoming light absorbed to achieve one or more given goals, such as to produce one molecule of oxygen, to fix one molecule of carbon dioxide, to incorporate one molecule of carbon into the cell for growing biomass, or the like, or combinations thereof). Using this pre-screening method can give greater assurance that altered strains, e.g., whether produced by directed evolution or by genetic means, can be hindered as little as possible by intrinsic (photosynthetic) inefficiencies. This pre-screening can advantageously reduce overall efforts and produce better results.

Additionally or alternately, strains can be pre-screened for increased photosynthetic productivity/efficiency by seeking strains with a lower pigment content—one advantageous test of lower pigment content utilizes a natural physiological state that most algal strains possess, namely a high light acclimated state. When most algae are exposed to either constant high light or varying light levels with greater than saturating average light intensity, the cells typically tend to lower their pigment content in response to high light intensity. This can generally be produced easily in a laboratory environment. The methods according to the present invention have been designed to select for strains that, when genetically encouraged to remain in a high light (low pigment) adapted state, can have higher productivity in dense mass culture under high incident light. In one embodiment, the method comprises an initial step in which algal cells are tested in their "normal," highly-pigmented state for their quantum efficiency. These cells are tested in relatively dilute culture and at a sub-saturating light intensity (<$I_s$). Though the limits of sub-saturating intensity can vary with different photosynthetic cells, sub-saturating light intensity can be less than about 200 $\mu E/m^2/s$, e.g., less than about 175 $\mu E/m^2/s$, less than about 150 $\mu E/m^2/s$, less than about 125 $\mu E/m^2/s$, less than about 100 $\mu E/m^2/s$, less than about 75 $\mu E/m^2/s$, less than about 60 $\mu E/m^2/s$, or less than about 50 $\mu E/m^2/s$; additionally or alternately, the light intensity to which the cells are exposed can be at least about 10 $\mu E/m^2/s$, e.g., at least about 25 $\mu E/m^2/s$, at least about 40 $\mu E/m^2/s$, at least about 50 $\mu E/m^2/s$, at least about 60 $\mu E/m^2/s$, at least about 75 $\mu E/m^2/s$, at least about 100 $\mu E/m^2/s$, at least about 125 $\mu E/m^2/s$, or at least about 150 $\mu E/m^2/s$.

In this pre-screening step, analysis can be conducted by any one or more of several methods, including but not limited to using the absorption spectrum of the algae and the initial slope of short term methods of measuring photosynthesis such as P-I (photosynthesis-irradiance) curves (e.g., based on oxygen evolution or radioactive carbon 14 dioxide uptake, or the like), fluorescence ETR curves, and/or qP curves. A preferred method of analysis can include measuring the quantum requirement for growth by growing optically thin cultures in front of light whose emission spectrum has been measured, then measuring the quanta absorbed by the algal culture/suspension from this emission spectrum and the absorption spectrum of the suspension, followed by measuring the carbon incorporated into the growing culture vis-à-vis the specific growth rate of the culture/suspension.

If the algal cells are found to exhibit relatively high quantum efficiency (relatively low quantum requirement, as quantum efficiency correlates with the reciprocal of quantum requirement), then the particular strain can advantageously be selected to proceed to the next step, as such strains can advantageously not be photosynthetically hindered and/or impaired in a way that cannot easily be remedied by lowering the attendant pigment content in the strain. By "relatively high quantum efficiency" and/or "relatively low quantum requirement", it should be understood that, for quantum requirements being sought relative to one molecule of oxygen evolution, to one mole carbon fixation/uptake, and/or to one mole of carbon incorporated into growing biomass, an ideal (substantially efficient) quantum requirement represents about 10-12. Therefore, a "relatively low" quantum requirement can advantageously be about 16 or less, e.g., about 15 or less, about 14 or less, or about 13 or less. As stated above, these relatively low quantum requirement strains can be said to have correspondingly (relatively) high quantum efficiency.

Optionally, before the pre-screening, wild type algal species can be pre-pre-screened, looking for strains that already exhibit certain characteristics consistent with high photosynthetic efficiency and with capability of further increasing it. If such a pre-pre-screen is not done, the possibility exists that certain intrinsic inefficiencies may preclude finding desirable photosynthetic mutants. For example, Photosynthesis-Irradiance (P-I) curves, based on oxygen evolution and/or carbon dioxide uptake, can be generated, as can actual growth experiments, and any combination of these can be used.

Since attempts are being made to increase cell efficiency by balancing photon absorption with photosynthetic capacity, one method can include starting with a strain that already exhibits relatively high photosynthetic capacity. This can minimize the degree to which cellular pigment needs to be reduced. $P_{max}$ per cellular mass from a P-I curves is one exemplary measure of the maximum photosynthetic rate, as is the maximum specific growth rate of a strain.

In one exemplary embodiment, using the P-I curves and/or specific growth rates-I curve, the saturating irradiance can be determined, which is defined as the intersection of the initial slope and the maximum rate (the limit at very high irradiances). One path forward can be to select for strains with a relatively high (e.g., the highest) saturating irradiance, again in order to reduce/minimize the degree of pigment reduction required. The best strains are typically ones in which the light curves approach the envelope formed by the extension of the initial slope to the maximum rate most closely.

Low respiration/maintenance rates can be determined by the light curves at approximately zero light or by growth curves extrapolated to zero light input. Respiration losses can typically be magnified in reduced pigment strains, especially under relatively low light conditions, where a greater proportion of the photons absorbed are typically used to maintain the biomass rather than to grow.

In some embodiments of the methods according to the invention, an optionally but preferably pre-screened candidate can be exposed in an optically thin culture to relatively high irradiance (>>$I_s$) until the cell's pigment (e.g., as measured by fluorescence spectroscopy or optical spectroscopy, for instance targeting chlorophyll content or extracted chlorophyll content, respectively, such as chlorophyll a content) is reduced by at least 50%, e.g., by at least 60%, by at least 67%, by at least 75%, by at least 80%, by at least 85%, by at least 90%, by about 50% to about 99.9%, by about 50% to about 99%, by about 50% to about 95%, by about 50% to about 90%, by about 50% to about 85%, by about 50% to about 80%, by about 50% to about 75%, by about 50% to about 67%, by about 60% to about 99.9%, by about 60% to about 99%, by about 60% to about 95%, by about 60% to about 90%, by about 60% to about 85%, by about 60% to about 80%, by about 60% to about 75%, by about 60% to about 67%, by about 67% to about 99.9%, by about 67% to about 99%, by about 67% to about 95%, by about 67% to about 90%, by about 67% to about 85%, by about 67% to about 80%, by about 67% to about 75%, by about 75% to about 99.9%, by about 75% to about 99%, by about 50% to about 95%, by about 50% to about 90%, by about 75% to about 85%, by about 75% to about 80%, by about 80% to about 99.9%, by about 80% to about 99%, by about 80% to about 95%, or by about 80% to about 90%. The relatively high irradiance/light intensity can be at least about 200 $\mu E/m^2/s$, e.g., at least about 400 $\mu E/m^2/s$, at least about 500 $\mu E/m^2/s$, at least about 600 $\mu E/m^2/s$, at least about 700 $\mu E/m^2/s$, at least about 800 $\mu E/m^2/s$, at least about 900 $\mu E/m^2/s$, at least about 1000 $\mu E/m^2/s$, at least about 1100 $\mu E/m^2/s$, at least about 1200 $\mu E/m^2/s$, at least about 1300 $\mu E/m^2/s$, at least about 1400 $\mu E/m^2/s$, at least about 1500 $\mu E/m^2/s$, or at least about 1600 $\mu E/m^2/s$; additionally or alternatively, the relatively high irradiance/light intensity can be less than about 2400 $\mu E/m^2/s$, e.g., less than about 2200 $\mu E/m^2/s$, less than about 2000 $\mu E/m^2/s$, less than about 1800 $\mu E/m^2/s$, less than about 1600 $\mu E/m^2/s$, less than about 1500 µE/m²/s, less than about 1400 µE/m²/s, less than about 1300 µE/m²/s, less than about 1200 µE/m²/s, less than about 1100 µE/m²/s, less than about 1000 µE/m²/s, less than about 900 µE/m²/s, less than about 800 µE/m²/s, less than about 700 µE/m²/s, or less than about 600 µE/m²/s, but still above $I_s$. The pigment reduction can advantageously and preferably correspond to a high light acclimated state of the alga. This high light acclimated algal culture can then be exposed to relatively low (sub-saturating) light intensity, typically again in an optically thin culture, to measure a quantum requirement, e.g., for incorporating carbon as cells grow (additionally or alternatively, for oxygen evolution and/or by carbon dioxide uptake), which can test to see whether the cells have maintained (or evidenced) their quantum efficiency in relatively low light. Testing the quantum requirement for growth can take longer, but it can be preferred in some embodiments, simply because it is a direct measurement of growth (instead of indirect or correlative of growth) and/or because it can be a better long-term predictor of performance.

In such embodiments of the methods according to the invention, the optically thin cultures of the cells in their high light acclimated state can optionally but preferably be further screened by their exposure to an illuminating program to simulate cell movement through less optically thin and more dense cultures (e.g., at surfaces near incident light and into depths away from incident light, with attendant shading from other cells). Such an illuminating program can include, e.g., an illumination simulator and methods of using same disclosed in International Publication No. WO 2013013139, the contents of which are hereby incorporated by reference in their entirety. The cells subject to such an illuminating plan can advantageously be tested for their biomass productivity by any one or more applicable tests, e.g., measuring the specific growth rate of the dilute suspension (under a short-term exposure, such as for less than 4 hours and/or for a short enough time so as not to substantially revert to the low light acclimated state, using a light profile changing with time to simulate the movement of cells through a dense culture whose light extinction is prescribed by K [in m$^{-1}$] in the simulation) and multiplying the specific growth rate by the biomass density determined in the simulation by dividing K by the absorption cross section per unit biomass of the dilute suspension. If the high light acclimated culture exhibits higher biomass productivity than its strain counterpart that has a higher level of pigmentation, then such a strain can advantageously pass the screening process and qualify as a potential candidate for a photosynthetic mutant.

Once potential candidate strains have passed the screening test methods described herein, they can be studied, e.g., to determine any genetic impact on their positive performance. A common tool for genetic study can include transcriptomics, although other tools can include, but are not limited to, bioinformatics, proteomics, genomics—any one or more of these can be utilized to determine genetic differences between the high light acclimated state and the low light acclimated state genotypes. Optionally, if genetic differences can be isolated and the coding for desirable traits (e.g., relatively low pigmentation, relatively high quantum efficiency, and/or regulation to produce such traits) can be determined, then one path forward can include artificial manipulation, e.g., by recombinant methods, to genetically engineer such desirable traits into model and/or selected organisms, for instance to form permanently low pigment strains that also have a low quantum requirement and preferably also exhibit relatively high biomass productivity (which can manifest, for example, as carbon fixation selectively being low in protein and high in carbohydrates and/or lipids). Additionally or alternatively, a potential photosynthetically efficient candidate strain (e.g., that exhibits both relatively low pigment and relatively high quantum efficiency) can be artificially manipulated, e.g., by genetic engineering, to exhibit no significant attendant loss in photosynthetic efficiency, preferably with relatively high biomass (and/or lipid and/or starch) productivity (e.g., without significant increase in pigment content and/or without significant increase/reduction in quantum requirement/efficiency, respectively).

However biomass productivity is measured, whether as weight per cell of all biomass, as weight per cell of carbohydrates, as weight per cell of lipids, as weight per cell of the combination of carbohydrates and lipids, or based on some other specific value, it can be desirable for the biomass productivity to be at least 25% higher (e.g., at least about 30% higher, at least about 40% higher, at least about 50% higher, at least about 60% higher, at least about 75% higher, at least about 100% higher, at least about 125% higher, at least about 150% higher, at least about 175% higher, at least about 200% higher, at least about 225% higher, at least about 250% higher, at least about 275% higher, at least about 300% higher, at least about 350% higher, at least about 400% higher, at least about 450% higher, or at least about 500% higher) in a candidate strain than in its corresponding wild type strain, than in a corresponding normal or relatively high pigment content strain, than in a corresponding normal or relatively low photosynthetically efficient strain, than in a corresponding strain having a normal or relatively low quantum efficiency, and/or than in a corresponding strain having a normal or relatively high quantum requirement.

Additionally or alternately, the high light acclimated state of a candidate algal strain can be induced and selected by growing such candidate strains in a photobioreactor (whether open, such as a pond, or closed) and by operating the photobioreactor at a fast enough rate of dilution (low enough cell density) for the average light intensity in the photobioreactor to be saturating or super-saturating. In some such embodiments, the photobioreactor can be operated at a relatively low standing biomass (e.g., less than about 30 g/m² in a pond) for at least 50% of the time during the day and/or for up to the entire day (e.g., which can include dilution at a rate of about 50% per day or more, particularly on warm sunny days). Such operation can advantageously induce the high light acclimated state in the algae, advantageously with all of its attendant benefits (higher photosynthetic efficiency, higher biomass productivity, higher oil and/or carbohydrate content, and the like), and optionally but preferably can additionally overcome one of the greatest deficiencies of normally produced photosynthetic mutants—lack of competitiveness versus low light (adapted) states (e.g., due to faster growth of the low light states under low intensity light environment of the photobioreactor, as normally operated). Of course, one disadvantage is that the relatively low density of the culture utilized to induce the high light acclimated state can make exploitation of the increased biomass harder to access, e.g., through more difficult cell harvesting (because of the additional medium necessary to be excluded during harvesting). Thus in this method of inducing the high light acclimated state, the photobioreactor can also test the potential for increasing biomass productivity in this state. In some embodiments, in addition to or instead of focusing merely on biomass productivity, strains can be pre-screened and/or selected using the inventive methods to find those that readily exhibit the high light acclimated state and that induce a relatively high (e.g., the highest) lipid and/or starch content, in absolute terms and/or in comparison to the (low light acclimated state of the) wild-type or parent strain(s). Exemplary tests for lipid productivity can include, but are not limited to, tests involving extraction and esterification to FAME (fatty acid methyl esters), modified Bligh-Dyer type tests, Bligh-Dyer type tests, Nile Red staining tests, and the like, and combinations thereof. Exemplary tests for starch productivity can include, but are not limited to, anthrone type tests, phenol-sulfuric acid type tests, iodine type tests, and the like, and combinations thereof.

There are many ways to make genetic alterations, some random, some targeted. One method for linking desirable traits to genes can include emulating and/or locking in the high light acclimated physiological state that many algal strains are able to attain when exposed to super-saturating light intensity for a prolonged period of time. One way of accomplishing this can be to maintain an optically thin algal culture/suspension under exposure to relatively high light intensity, e.g., by diluting it often enough to prevent the light at the darkest part of the suspension from becoming less than saturating. These high light acclimated states can advantageously exhibit at least some of low pigment content per cell, high saturating irradiance, high photosynthetic capacity, and high quantum efficiency under sub-saturating light, inter alia. One preferred way to target desired genetic alterations in a mutant strain can be to test the high light acclimated state of wild type strains as follows. It can be desirable, in some embodiments, to double check that there is not more than a minor (preferably no) decrease in maximum efficiency of conversion of light to biomass occurring and/or to confirm that the respiratory/maintenance rate has not increased significantly (preferably not at all) as a consequence of the genetic alteration. Each step herein can be a further enabler of the others for attaining appropriate candidates, but they need not be in any particular order, except where noted.

1. Measuring the quantum efficiency of the relatively low light (sub-saturating) adapted state to make sure it is high enough.
2. Adapting the strain(s) to high light intensity, e.g., using at least three times (for instance, at least four times, at least five times, at least six times, or at least ten times) the saturating irradiance sufficient to attain at least a halving (e.g., at least a two thirds reduction in) of chlorophyll a content/formation.
3. Measuring the quantum efficiency of the high light acclimated state in relatively low (sub-saturating) light intensity, e.g., to make sure it is at least 75% of the quantum efficiency of the low light acclimated state as measured in step 1 above, and/or measuring $P_{max}$ per unit cell mass of the high light acclimated state, e.g., to make sure it is at least 75% of the value for the relatively low (sub-saturating) light acclimated state. In order to be effective in assessing the high light acclimated state, such measurement(s) should be done in a short enough time so that the cells do not significantly revert back to their low light acclimated state during the measurement(s).
4. Optionally but preferably validating that higher photosynthetic efficiency is attained by the high light acclimated culture versus the relatively low (sub-saturating) light acclimated culture, e.g., by growing both (for a short enough time such that little or substantially no significant change in adaptation state occurs) in optically thin suspensions under a light regime that simulates (e.g., by use of programmable lights) movement of cells in a dense suspension illuminated with super-saturating light intensities (e.g., in one embodiment, about 500 µE/m$^2$/s to about 3000 µE/m$^2$/s or about 900 µE/m$^2$/s to about 2500 µE/m$^2$/s).
5. Optionally validating that higher photosynthetic efficiency is attained by the high light acclimated culture versus the low light acclimated culture by growing both (for a short enough time such that little or substantially no significant change in adaptation state occurs) in optically thin suspensions in a pond, or any photobioreactor, by adjusting dilution rate such that, when the incident irradiance is saturating, the average irradiance within the pond is also saturating (e.g., in one embodiment, about 900 µE/m$^2$/s to about 2500 µE/m$^2$/s to approximate solar noon).

These strains or states can be selected for and/or induced in the laboratory by using the algal illuminator or similar device which allows dilute suspensions of algae to be illuminated by programmable lights to simulate the light exposure of cells in the mass culture, thereby selecting for the same highly efficient strains and/or inducing the highly efficient light adaptation state. Additionally or alternatively, such programmable light regimes may be used to impose conditions that select for strains and/or that induce states more resistant to photoinhibition.

EMBODIMENTS ACCORDING TO THE INVENTION

Additionally or alternatively, the present invention can include one or more of the following. These can be individual (solitary) or can be combined with any one or more others listed below, as well as with any one or more others listed herein.

1. First wild types can be pre-screened, looking for strains which already have characteristics consistent with high photosynthetic efficiency and further increasing it. Otherwise intrinsic inefficiencies may preclude further increasing efficiency. Photosynthesis-Irradiance (P-I) curves, based on oxygen evolution or carbon dioxide uptake, can be used additionally or alternatively to actual growth experiments.

a. High quantum efficiency (low quantum requirement) under sub-saturating light can be advantageous. One can measure an output (oxygen evolved, carbon dioxide taken up, or growth, per unit biomass per unit time) divided by the amount of light absorbed per unit biomass per unit time. The input can be determined from the emission spectra of the lights used and absorption spectra of the algal suspension.

b. At high light, absorption can far outstrip photosynthetic capacity (light saturation), resulting in inefficiencies that are to overcome using these methods. Since one is typically trying to increase efficiency by balancing absorption with photosynthetic capacity, one option can be to start with strains that already have high photosynthetic capacity. This can lessen/minimize the degree to which cellular pigment should be reduced. $P_{max}$ from the P-I curves can be a measure of the maximum photosynthetic rate, as can be the maximum specific growth rate of a strain.

c. From the P-I curve and/or the specific growth rate-I curve, one can determine the saturating irradiance, defined as the intersection of the initial slope and the maximum rate. One can look for strains with the highest saturating irradiance, again in order to lessen/minimize the impact of/need for pigment reduction. This can usually be determined by a and b above, but the best strains can typically be ones where the light curves approach the envelope formed by the extension of the initial slope to the maximum rate most closely.
   d. Low respiration or maintenance rates can be determined by the light curves at approximately zero light and/or by growth curves extrapolated to zero light input. Respiration losses can be magnified in reduced pigment strains, especially under low light where a greater proportion of the photons absorbed must be used to maintain the biomass rather than to grow.
2. The screening/selecting of the multitude of mutant strains produced by whatever method which was used to genetically alter the wild type (or parent) can be improved. Screening can include looking for low cellular pigment which stays low in low light, higher saturating irradiance than the progenitor parent (determined from P-I curves, fluorescence ETR curves, qP curves, and/or any other measurement), and little or no diminishment of photosynthetic capacity.
In addition, it can be advantageous to maintain as many as possible of the positive characteristics listed above in the pre-screening.
   a. A further screen can be to measure the quantum efficiency of the mutants under sub-saturating light by one or more of the methods described herein to make sure that no unacceptable/significant decrease in maximum efficiency of conversion of light to biomass has occurred as a consequence of the genetic alteration.
   b. Also, it can be advantageous to measure the respiratory and/or maintenance rate, to make sure it has not unacceptably/significantly increased.
3. The high light acclimated physiological state of the candidate wild type (parent) algal strain can be assessed for its suitability vis-à-vis the pigment reduction process.
   a. The quantum efficiency of the low light (subsaturating) adapted state can be measured to make sure it is high (0.067 or more moles of carbon incorporated during growth per moles of photons absorbed, corresponding to a quantum requirement of 15 or less moles of photons absorbed per moles of carbon incorporated during growth).
   b. The cells can be adapted to high light using a super-saturating irradiance, for example at about five times the saturating irradiance, attaining at least two thirds reduction in mass of chlorophyll a per cell mass.
   c. The specific growth rate of the cells in the high light acclimated state in high light can be measured to make sure the photosynthetic capacity of the high light acclimated state is sufficiently high. The specific growth rate can preferably be at least three times higher than that of the low light acclimated state, and/or the $P_{max}$ per unit cell mass can typically be at least 75% of the relatively low light (sub-saturating) adapted state of the wild-type or parent.
   d. The quantum efficiency of the high light acclimated state in low (sub-saturating) light can be measured to make sure it is at least 75% (e.g., at least 80%, at least 85%, at least 90%, at least 95%, at least 100%, at least 110%, or at least 125%) of the quantum efficiency of the relatively low (sub-saturating) light acclimated state as measured in 3a (if the quantum requirement is measured in 3a, then the quantum requirement of the high light acclimated state in low light can be at most 125%, e.g., at most 120%, at most 115%, at most 110%, at most 105%, at most 100%, at most 90%, or at most 75%, of that of the relatively low light acclimated state). This measurement should typically be done in a time short enough so that the cells do not significantly adapt back to low light.
   e. A higher photosynthetic efficiency attained by the high light acclimated culture versus the low light acclimated culture can be validated, in one embodiment by growing both (for a short enough time that little or no change in state of adaptation occurs, e.g., less than 4 hours or less than 3 hours) in optically thin suspensions (e.g., in which at most 30% of light/photons are absorbed by the culture, such as at most 25%, at most 20%, at most 15%, at most 10%, or at most 5%) in front of programmable light under a light regime programmed to simulate the movements of cells in a dense suspension (e.g., in which at least 70% of light/photons are absorbed by the culture, such as at least 75%, at least 80%, at least 85%, at least 90%, at least 95%, at least 99%; additionally or alternately, about 100% of the light/photons are absorbed by up to 99% of the culture, such as up to 95%, up to 90%, up to 85%, up to 80%, up to 75%, up to 70%, up to 60%, up to 50%, up to 40%, up to 25%, or up to 10%), which cells/culture are/is illuminated with high light (e.g., from about 900 μE/m²/s to about 2500 uE/m²/s). This higher photosynthetic efficiency can be attained when the biomass productivity (e.g., ash-free dry weight per volume of culture per unit time and/or ash-free dry weight per area of illuminated surface of the culture per unit time) of the high light acclimated culture (high light acclimated wild-type and/or parent strains) is at least 25% higher (at least 35% higher, at least 50% higher, at least 75% higher, or at least 100% higher) than that of the low light acclimated culture (wild-type and/or parent strains).
4. The genetic changes to be made to reduce cellular pigment can be modeled after the genetic differences observed between the high light acclimated state (which can advantageously meet the criteria in 3) and the low light acclimated state of the wild-type and/or parent algal strain. Many methods to do this can include, but are not limited to, comparative 'omics technology, including transcriptomics, proteomics, metabolomics, genomics, and the like, and combinations thereof.
5. High light acclimated states typically not only have low cellular pigment, but also much reduced protein content and/or much higher carbohydrate/lipid content. Thus, these high light acclimated states can also/alternately be used to determine, as in 4, the genetic changes needed to produce such a change of composition.
6. High light acclimated states, typically having the desirable properties of low pigment, higher photosynthetic efficiency, and high storage product content, can in some embodiments be produced in a pond (or other photo bioreactor) by operating at low standing biomass (e.g., less than 30 g/m²) in a pond, for all or at least 50% of the time during the day (e.g., diluted at a rate of 50% per day or more, such as on warm, very sunny days).
7. Additionally or alternatively, strains can be pre-screened, for instance using the method in 3, especially when 3e is operated to simulate the optically thin suspensions described in 6, to find those that are promising examples of desirable benefits of the high light acclimated state (low pigment content, highest photosynthetic efficiency) and/or optionally that induce an interestingly high (the highest) lipid and/or carbohydrate content.

8. Additionally or alternatively, strains can be adapted/selected for certain characteristics using the algal illuminator to simulate the high light environment of a dilute suspension in a pond (or other photo bioreactor), and for further positive traits such as resistance to photo-inhibition and greater storage product content.

OTHER EMBODIMENTS

Additionally or alternately, the present invention can include a method for determining and/or engineering photosynthetic mutant algal strains comprising: (A) pre-screening wild-type or parent strains to select for photosynthetic efficiency by (1) measuring a quantum requirement of said wild-type or parent strains at a sub-saturating light intensity; (2) for wild-type or parent strains having a relatively low quantum requirement, further measuring photosynthetic capacity to select for strains having a relatively high $P_{max}$, which includes a $P_{max}$ for oxygen evolution of at least about 100 nmol/mg dry weight/minute (e.g., at least about 110 nmol/mg dry weight/minute, at least about 120 nmol/mg dry weight/minute, at least about 130 nmol/mg dry weight/minute, at least about 140 nmol/mg dry weight/minute, at least about 150 nmol/mg dry weight/minute, at least about 160 nmol/mg dry weight/minute, from about 100 nmol/mg dry weight/minute to about 300 nmol/mg dry weight/minute, from about 100 nmol/mg dry weight/minute to about 250 nmol/mg dry weight/minute, from about 100 nmol/mg dry weight/minute to about 225 nmol/mg dry weight/minute, from about 120 nmol/mg dry weight/minute to about 300 nmol/mg dry weight/minute, from about 120 nmol/mg dry weight/minute to about 250 nmol/mg dry weight/minute, from about 120 nmol/mg dry weight/minute to about 225 nmol/mg dry weight/minute, from about 140 nmol/mg dry weight/minute to about 300 nmol/mg dry weight/minute, from about 140 nmol/mg dry weight/minute to about 250 nmol/mg dry weight/minute, or from about 140 nmol/mg dry weight/minute to about 225 nmol/mg dry weight/minute), a $P_{max}$ for carbon fixation of at least about 80 nmol/mg dry weight/minute (e.g., at least about 90 nmol/mg dry weight/minute, at least about 100 nmol/mg dry weight/minute, at least about 110 nmol/mg dry weight/minute, at least about 120 nmol/mg dry weight/minute, at least about 130 nmol/mg dry weight/minute, at least about 140 nmol/mg dry weight/minute, at least about 150 nmol/mg dry weight/minute, at least about 160 nmol/mg dry weight/minute, from about 80 nmol/mg dry weight/minute to about 300 nmol/mg dry weight/minute, from about 80 nmol/mg dry weight/minute to about 250 nmol/mg dry weight/minute, from about 80 nmol/mg dry weight/minute to about 200 nmol/mg dry weight/minute, from about 100 nmol/mg dry weight/minute to about 300 nmol/mg dry weight/minute, from about 100 nmol/mg dry weight/minute to about 250 nmol/mg dry weight/minute, from about 100 nmol/mg dry weight/minute to about 200 nmol/mg dry weight/minute, from about 110 nmol/mg dry weight/minute to about 300 nmol/mg dry weight/minute, from about 110 nmol/mg dry weight/minute to about 250 nmol/mg dry weight/minute, from about 110 nmol/mg dry weight/minute to about 200 nmol/mg dry weight/minute, from about 130 nmol/mg dry weight/minute to about 300 nmol/mg dry weight/minute, from about 130 nmol/mg dry weight/minute to about 250 nmol/mg dry weight/minute, from about 130 nmol/mg dry weight/minute to about 200 nmol/mg dry weight/minute, from about 140 nmol/mg dry weight/minute to about 300 nmol/mg dry weight/minute, from about 140 nmol/mg dry weight/minute to about 250 nmol/mg dry weight/minute, or from about 140 nmol/mg dry weight/minute to about 200 nmol/mg dry weight/minute), a $\mu_{max}$ of at least about 0.08 hr$^{-1}$ (e.g., at least about 0.1 hr$^{-1}$, at least about 0.125 hr$^{-1}$, at least about 0.15 hr$^{-1}$, at least about 0.167 hr$^{-1}$, at least about 0.18 hr$^{-1}$, at least about 0.208 hr$^{-1}$, from about 0.1 hr$^{-1}$ to about 0.25 hr$^{-1}$, from about 0.1 hr$^{-1}$ to about 0.208 hr$^{-1}$, from about 0.125 hr$^{-1}$ to about 0.25 hr$^{-1}$, or from about 0.125 hr$^{-1}$ to about 0.208 hr$^{-1}$), or a combination thereof; (3) optionally further measuring a saturating light intensity on strains satisfying the requirements of (A)(1) and A(2) to screen for strains whose $I_s$ is relatively high (e.g., at least 125 µE/m$^2$/s, at least 150 µE/m$^2$/s, or at least 175 µE/m$^2$/s); (4) optionally further measuring a respiration and/or maintenance rate on strains satisfying the requirements of (A)(1) and A(2), and optionally also (A)(3), to screen for strains whose respiration/maintenance rate is less than 10% of $\mu_{max}$ and/or $P_{max}$, wherein the pre-screening results in a group of wild-type and/or parent strains for further study; and (5) optionally producing a high light acclimated state in the wild-type or parent, which wild-type or parent passes (A)(1) and (A)(2) and optionally (A)(3) and optionally (A)(4) to determine whether the high light acclimated wild-type or parent: (a) has at least a two thirds reduction in mass of chlorophyll a per cell mass; (b) has $P_{max}$ per cell mass within 20% of the relatively low light (sub-saturating) adapted state of the wild-type or parent; (c) has an $I_s$ of at least 250 µE/m$^2$/s; and (d) has a quantum requirement in a short term test under sub-saturating light of at most 125% of the wild-type or parent strain in a short term test under sub-saturating light; (B) cause genetic mutations in the group of wild-type and/or parent strains from pre-screening (A) to form genetic mutant strains; (C) screening the genetic mutant strains for photosynthetic efficiency in mass cultures by (1) measuring a pigment content (e.g., total chlorophyll content and/or chlorophyll a content) in said genetic mutant strains; (2) for genetic mutant strains having a pigment content that is reduced by at least about 50%, as compared to a pigment content of its corresponding wild-type and/or parent strain, further measuring photosynthetic capacity to select for strains having a relatively high $P_{max}$ per cellular mass, as compared to the $P_{max}$ per cellular mass of its corresponding wild-type and/or parent strain (e.g., not more than about 25% lower than, or alternately within about 25% of, the $P_{max}$ per cellular mass of its corresponding wild-type and/or parent strain); (3) for genetic mutant strains satisfying both (C)(1) and (C)(2), measuring saturating light intensity, $I_s$, to select for strains whose $I_s$ is relatively high in and of itself (e.g., at least 250 µE/m$^2$/s, at least 350 µE/m$^2$/s, at least 500 µE/m$^2$/s, or at least 600 µE/m$^2$/s) and/or whose $I_s$ is at least twice that of its corresponding wild-type and/or parent strain; (4) for genetic mutant strains satisfying (C)(1)-(C)(3), measuring a quantum requirement at a sub-saturating light intensity to select for strains having a relatively low quantum requirement, by itself (e.g., 15 or less, 14 or less, or 13 or less), and/or at most 125% (e.g., at most 120%, at most 115%, at most 110%, at most 105%, at most 100%, at most 90%, or at most 75%) of the quantum requirement of its corresponding wild-type and/or parent strain; and (5) optionally, for genetic mutant strains satisfying (C)(1)-(C)(4), further measuring a respiration and/or maintenance rate to screen for strains whose respiration/maintenance rate is less than 10% of $\mu_{max}$ and/or $P_{max}$; and (D) further screening the genetic mutants resulting from screening (C) (i) by measuring biomass productivity to select strains having relatively high biomass productivity (e.g., whose ash-free dry weight per volume of culture per unit time and/or whose ash-free dry weight per area of illuminated surface of the culture per unit time is at least 25% higher, e.g., at least 30% higher, at least 40% higher, at least 50% higher, at least 75% higher, or at least 100% higher, than that of the wild-type and/or parent strains), (ii) by measuring lipid and/or starch productivity to select mutant strains having a lipid productivity and/or a starch productivity that is at least 25% higher than that of the corresponding wild-type and/or parent strains, or (iii) both (i) and (ii).

In the embodiment above, step (A)(5) can be accomplished in a laboratory illuminator with a culture volume of the wild type or parent being diluted such that a majority of the culture volume is above $I_s$ when exposed to a source of incident light (e.g., with at least 5% of incident light reaching a surface of the illuminator opposite the source of incident light, such as at least 10%, at least 15%, at least 20%, at least 30%, at least 40%, or at least 50%), thereby resulting in the high light acclimated wild type or parent having a chlorophyll a content per unit cell mass at least 25% lower (e.g., at least 35% lower, at least 50% lower, at least 75% lower, or at least 90% lower) relative to that of the wild-type or parent cultured under sub-saturating light conditions for the same period. Additionally or alternatively, step (A)(5) can be accomplished in an open pond with a culture volume of the wild type or parent being diluted such that a majority of the culture volume is at or above light saturation when exposed to a source of incident light (e.g., with at least 5% of incident light reaching a bottom of the open pond, such as at least 10%, at least 15%, at least 20%, at least 30%, at least 40%, or at least 50%), thereby resulting in the high light acclimated wild type or parent having a chlorophyll a content per unit cell mass lower (e.g., at least 15% lower, at least 25% lower, at least 35% lower, at least 50% lower, at least 75% lower, or at least 90% lower) than that of the wild-type or parent in a typically diluted culture (e.g., dilution of 80% per day or less, of 70% per day or less, of 60% per day or less, or 50% per day or less) in which the cells have a chlorophyll a content per unit cell mass similar to that of the parent culture adapted to low/sub-saturating light.

In any or all of the embodiments above, either step (B) comprises or the method further comprises a step between steps (B) and (C) that comprises: probing changes in genetic expression exhibited by the high light acclimated wild type or parent that are not present in the wild type or parent prior to production of the high light acclimated state in the wild type or parent.

In any or all of the embodiments above, prior to step (B), a high light acclimated wild-type or parent strain produced in step (A)(5) can be validated in a laboratory illuminator by growing both the high light acclimated wild-type or parent strain and the wild-type or parent strain for less than 4 hours in optically thin suspensions in front of programmable light under a light regime programmed to simulate the movements of cells in a dense suspension, which cells/culture are/is illuminated with from about 900 µE/m²/s to about 2500 µE/m²/s to achieve a biomass productivity of the high light acclimated wild-type or parent strain that is at least 25% higher than that of the wild-type and/or parent strain.

Although the present invention has been described in terms of specific embodiments, it need not necessarily be so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:

1. A method for determining and/or engineering photosynthetic mutant algal strains comprising:
   (A) pre-screening wild-type or parent strains to select for photosynthetic efficiency by
      (1) measuring a quantum requirement of said wild-type or parent strains at a sub-saturating light intensity;
      (2) for wild-type or parent strains having a quantum requirement of 15 or less, further measuring photosynthetic capacity to select for strains having a relatively high $P_{max}$ per cellular mass, which includes a $P_{max}$ per cellular mass for oxygen evolution of at least about 100 nmol/mg dry weight/minute, a $P_{max}$ per cellular mass for carbon fixation of at least about 80 nmol/mg dry weight/minute, a $\mu_{max}$ for specific growth rate of at least about 0.1 hr$^{-1}$, or a combination thereof;
      (3) optionally further measuring a saturating light intensity on strains satisfying the requirements of (A)(1) and A(2) to screen for strains whose $I_s$ is at least 125 µE/m²/s;
      (4) optionally further measuring a respiration and/or maintenance rate on strains satisfying the requirements of (A)(1) and A(2), and optionally also (A)(3), to screen for strains whose respiration/maintenance rate is less than 10% of $\mu_{max}$ and/or $P_{max}$, wherein the pre-screening results in a group of wild-type and/or parent strains for further study; and
      (5) producing a high light acclimated state in the wild-type or parent, which wild-type or parent passes (A)(1) and (A)(2) and optionally (A)(3) and optionally (A)(4) to determine whether the high light acclimated wild-type or parent:
         (a) has at least a two thirds reduction in mass of chlorophyll a per cell mass;
         (b) has $P_{max}$ per cell mass within 20% of $P_{max}$ per cell mass of the relatively low light (sub-saturating) adapted state of the wild-type or parent;
         (c) has an $I_s$ of at least 250 µE/m²/s; and
         (d) has a quantum requirement in a short term test under sub-saturating light of at most 125% of the wild-type or parent strain in a short term test under sub-saturating light;
   (B) cause genetic mutations in the group of wild-type and/or parent strains from pre-screening (A) to form genetic mutant strains;
   (C) screening the genetic mutant strains for photosynthetic efficiency in mass cultures by
      (1) measuring a pigment content in said genetic mutant strains;
      (2) for genetic mutant strains having a pigment content that is reduced by at least about 50%, as compared to a pigment content of its corresponding wild-type and/or parent strain, further measuring photosynthetic capacity to select for strains having a relatively high $P_{max}$ per cellular mass, that is at least 75% of a $P_{max}$ per cellular mass of its corresponding wild-type and/or parent strain;
      (3) for genetic mutant strains satisfying both (C)(1) and (C)(2), measuring saturating light intensity, $I_s$, to select for strains whose $I_s$ is at least 250 µE/m²/s and/or whose $I_s$ is at least twice that of its corresponding wild-type and/or parent strain;
      (4) for genetic mutant strains satisfying (C)(1)-(C)(3), measuring a quantum requirement at a sub-saturating light intensity to select for strains having a quantum requirement of 15 or less and/or at most 125% of the quantum requirement of its corresponding wild-type and/or parent strain; and
  (5) optionally, for genetic mutant strains satisfying (C)(1)-(C)(4), further measuring a respiration and/or maintenance rate to screen for strains whose respiration/maintenance rate is less than 10% of $\mu_{max}$ and/or $P_{max}$ per cellular mass; and
(D) further screening the genetic mutants resulting from screening (C) by measuring biomass productivity to select strains having relatively high biomass productivity, measured as ash-free dry weight per volume of culture per unit time and/or as ash-free dry weight per area of illuminated surface of the culture per unit time, at least 25% higher than that of the corresponding wild-type and/or parent strains.

2. The method of claim 1, wherein step (A)(5) is accomplished in a laboratory illuminator with a culture volume of the wild type or parent being diluted such that a majority of the culture volume is above $I_s$ when exposed to a source of incident light, thereby resulting in the high light acclimated wild type or parent having a chlorophyll a content per unit cell mass at least 25% lower relative to that of the wild-type or parent cultured under sub-saturating light conditions for the same period.

3. The method of claim 1, wherein step (A)(5) is accomplished in an open pond with a culture volume of the wild type or parent being diluted such that a majority of the culture volume is at or above light saturation when exposed to a source of incident light, thereby resulting in the high light acclimated wild type or parent having a chlorophyll a content per unit cell mass at least 25% lower than that of the wild-type or parent in a typically diluted culture in which the cells have a chlorophyll a content per unit cell mass similar to that of the parent culture adapted to subsaturating light or less.

4. The method of claim 1, either wherein step (B) further comprises or wherein the method further comprising a step between steps (B) and (C) that comprises probing for changes in genetic expression exhibited by the high light acclimated wild type or parent that are not present in the wild type or parent prior to production of the high light acclimated state in the wild type or parent.

5. The method of claim 1, further comprising, prior to step (B), validating a high light acclimated wild-type or parent strain produced in step (A)(5) in a laboratory illuminator by growing both the high light acclimated wild-type or parent strain and the wild-type or parent strain for less than 4 hours in optically thin suspensions in front of programmable light under a light regime programmed to simulate the movements of cells in a dense suspension, which cells/culture are/is illuminated with from about 900 $\mu E/m^2/s$ to about 2500 $\mu E/m^2/s$ to achieve a biomass productivity of the high light acclimated wild-type or parent strain that is at least 25% higher than that of the wild-type and/or parent strain.

6. A method for determining and/or engineering photosynthetic mutant algal strains comprising:
(A) pre-screening wild-type or parent strains to select for photosynthetic efficiency by
  (1) measuring a quantum requirement of said wild-type or parent strains at a sub-saturating light intensity;
  (2) for wild-type or parent strains having a quantum requirement of 15 or less, further measuring photosynthetic capacity to select for strains having a relatively high $P_{max}$ per cellular mass, which includes a $P_{max}$ per cellular mass for oxygen evolution of at least about 100 nmol/mg dry weight/minute, a $P_{max}$ per cellular mass for carbon fixation of at least about 80 nmol/mg dry weight/minute, a $\mu_{max}$ for specific growth rate of at least about 0.1 $hr^{-1}$, or a combination thereof;
  (3) optionally further measuring a saturating light intensity on strains satisfying the requirements of (A)(1) and A(2) to screen for strains whose $I_s$ is at least 125 $\mu E/m^2/s$;
  (4) optionally further measuring a respiration and/or maintenance rate on strains satisfying the requirements of (A)(1) and A(2), and optionally also (A)(3), to screen for strains whose respiration/maintenance rate is less than 10% of $\mu_{max}$ and/or $P_{max}$, wherein the pre-screening results in a group of wild-type and/or parent strains for further study; and
  (5) producing a high light acclimated state in the wild-type or parent, which wild-type or parent passes (A)(1) and (A)(2) and optionally (A)(3) and optionally (A)(4) to determine whether the high light acclimated wild-type or parent:
    (a) has at least a two thirds reduction in mass of chlorophyll a per cell mass;
    (b) has $P_{max}$ per cell mass within 20% of $P_{max}$ per cell mass of the relatively low light (sub-saturating) adapted state of the wild-type or parent;
    (c) has an $I_s$ of at least 250 $\mu E/m^2/s$; and
    (d) has a quantum requirement in a short term test under sub-saturating light of at most 125% of the wild-type or parent strain in a short term test under sub-saturating light;
(B) cause genetic mutations in the group of wild-type and/or parent strains from pre-screening (A) to form genetic mutant strains;
(C) screening the genetic mutant strains for photosynthetic efficiency in mass cultures by
  (1) measuring a pigment content in said genetic mutant strains;
  (2) for genetic mutant strains having a pigment content that is reduced by at least about 50%, as compared to a pigment content of its corresponding wild-type and/or parent strain, further measuring photosynthetic capacity to select for strains having a relatively high $P_{max}$ per cellular mass, that is at least 75% of a $P_{max}$ per cellular mass of its corresponding wild-type and/or parent strain;
  (3) for genetic mutant strains satisfying both (C)(1) and (C)(2), measuring saturating light intensity, $I_s$, to select for strains whose $I_s$ is at least 125 $\mu E/m^2/s$ and/or whose $I_s$ is at least twice that of its corresponding wild-type and/or parent strain;
  (4) for genetic mutant strains satisfying (C)(1)-(C)(3), measuring a quantum requirement at a sub-saturating light intensity to select for strains having a quantum requirement of 15 or less and/or at most 125% of the quantum requirement of its corresponding wild-type and/or parent strain; and
  (5) optionally, for genetic mutant strains satisfying (C)(1)-(C)(4), further measuring a respiration and/or maintenance rate to screen for strains whose respiration/maintenance rate is less than 10% of $\mu_{max}$ and/or $P_{max}$ per cellular mass; and
(D) further screening the genetic mutants resulting from screening (C) by measuring lipid and/or starch productivity to select mutant strains having a lipid productivity and/or a starch productivity that is at least 25% higher than that of the corresponding wild-type and/or parent strains.

* * * * *